(12) United States Patent
Piecuch

(10) Patent No.: US 11,458,228 B2
(45) Date of Patent: Oct. 4, 2022

(54) MONOLITHIC COMPOSITE ORTHOPEDIC IMPLANTS AND ASSOCIATED METHODS

(71) Applicant: Zimmer, Inc., Warsaw, IN (US)

(72) Inventor: Cristina Piecuch, Winona Lake, IN (US)

(73) Assignee: Zimmer, Inc., Warsaw (IN)

( * ) Notice: Subject to any disclaimer, the term of this patent is extended or adjusted under 35 U.S.C. 154(b) by 483 days.

(21) Appl. No.: 16/567,625

(22) Filed: Sep. 11, 2019

(65) Prior Publication Data

US 2020/0000974 A1 Jan. 2, 2020

Related U.S. Application Data

(62) Division of application No. 15/689,455, filed on Aug. 29, 2017, now Pat. No. 10,441,684.

(60) Provisional application No. 62/385,541, filed on Sep. 9, 2016.

(51) Int. Cl.
| | | |
|---|---|---|
| A61L 31/02 | (2006.01) | |
| A61L 27/04 | (2006.01) | |
| A61L 27/06 | (2006.01) | |
| A61F 2/36 | (2006.01) | |
| C04B 35/488 | (2006.01) | |
| C04B 41/52 | (2006.01) | |

(52) U.S. Cl.
CPC ............... *A61L 31/022* (2013.01); *A61F 2/36* (2013.01); *A61L 27/045* (2013.01); *A61L 27/047* (2013.01); *A61L 27/06* (2013.01); *C04B 35/488* (2013.01); *C04B 41/52* (2013.01)

(58) Field of Classification Search
CPC ...... A61L 31/022; A61L 27/06; A61L 27/045; A61L 27/36
See application file for complete search history.

(56) References Cited

U.S. PATENT DOCUMENTS

| | | |
|---|---|---|
| 9,034,048 B2 | 5/2015 | Choren |
| 10,441,684 B2 | 10/2019 | Piecuch |
| 2005/0123672 A1 | 6/2005 | Justin et al. |
| 2006/0129240 A1 | 6/2006 | Lessar et al. |
| 2007/0142914 A1 | 6/2007 | Jones et al. |
| 2010/0161030 A1 | 6/2010 | Bayer et al. |

(Continued)

FOREIGN PATENT DOCUMENTS

| | | |
|---|---|---|
| CN | 102906017 A | 1/2013 |
| WO | WO-2018048673 A1 | 3/2018 |

OTHER PUBLICATIONS

"U.S. Appl. No. 15/689,455, Final Office Action dated Mar. 18, 2019", 8 pgs.

(Continued)

*Primary Examiner* — Jason-Dennis N Stewart
(74) *Attorney, Agent, or Firm* — Schwegman Lundberg & Woessner, P.A.

(57) ABSTRACT

Implementations described herein provide for functionless monolithic composite implants and methods for manufacturing the same. The implant includes a monolithic composite body having a first region comprising a first metal alloy, a second region comprising a second metal alloy, and a transition region disposed between the first region and the second region formed from a bonded mixture of the first alloy and the second alloy. In one example, the transition region is a sintered mixture of the first alloy and the second alloy. In another example, the transition region is disposed at a region of minimum stress within the monolithic composite body under physiological loading conditions of the implant.

20 Claims, 2 Drawing Sheets

(56) References Cited

U.S. PATENT DOCUMENTS

| | | |
|---|---|---|
| 2011/0022158 A1 | 1/2011 | Atanasoska et al. |
| 2012/0083896 A1 | 4/2012 | Kellar et al. |
| 2012/0095569 A1 | 4/2012 | Kellar et al. |
| 2012/0265319 A1 | 10/2012 | Prybyla et al. |
| 2013/0216420 A1 | 8/2013 | Li et al. |
| 2015/0012109 A1 | 1/2015 | Moreau |
| 2018/0071437 A1 | 3/2018 | Piecuch |

OTHER PUBLICATIONS

"U.S. Appl. No. 15/689,455, Non Final Office Action dated Jan. 24, 2019", 7 pgs.

"U.S. Appl. No. 15/689,455, Notice of Allowance dated Jun. 10, 2019", 7 pgs.

"U.S. Appl. No. 15/689,455, Response filed Feb. 28, 2019 to Non Final Office Action dated Jan. 24, 2019", 11 pgs.

"U.S. Appl. No. 15/689,455, Response filed May 13, 2019 to Final Office Action dated Mar. 18, 2019", 11 pgs.

"U.S. Appl. No. 15/689,455, Response filed Dec. 17, 2018 to Restriction Requirement mailed Oct. 19, 2018", 6 pgs.

"U.S. Appl. No. 15/689,455, Restriction Requirement dated Oct. 19, 2018", 6 pgs.

"International Application Serial No. PCT/US2017/049078, International Preliminary Report on Patentability dated Mar. 21, 2019", 8 pgs.

"International Application Serial No. PCT/US2017/049078, International Search Report dated Nov. 23, 2017", 4 pgs.

"International Application Serial No. PCT/US2017/049078, Written Opinion dated Nov. 23, 2017", 8 pgs.

"European Application Serial No. 17765514.9, Communication Pursuant to Article 94(3) EPC dated Mar. 1, 2021", 8 pgs.

"European Application Serial No. 17765514.9, Communication Pursuant to Article 94(3) EPC dated Apr. 17, 2020", 7 pgs.

"European Application Serial No. 17765514.9, Response filed Aug. 27, 2020 to Communication Pursuant to Article 94(3) EPC dated Apr. 17, 2020", 13 pgs.

"European Application Serial No. Response to Communication pursuant to Rules 161(1) and 162 EPC filed Nov. 4, 2019", 8 pgs.

MONOLITHIC COMPOSITE ORTHOPEDIC IMPLANTS AND ASSOCIATED METHODS

RELATED APPLICATIONS

This application is a divisional of U.S. patent application Ser. No. 15/689,455, filed Aug. 29, 2017, which claims the benefit of priority to U.S. Provisional Patent Application Ser. No. 62/385,541, filed Sep. 9, 2016, the content of each of which is incorporated herein by reference.

FIELD

The present disclosure relates to monolithic composite orthopedic implants comprised of at least two metal alloys and methods for manufacturing the same.

BACKGROUND

This section provides background information related to the present disclosure, which is not necessarily prior art.

Implant debris of any kind can result in patient complications. In one example, implants with metal-on-metal bearing surfaces or junctions can release metal debris and/or ions into the body of a patient. This can result from one or more of wear, fretting, corrosion, and fretting corrosion at implant interfaces and/or junctions. Such implant debris can lead to various adverse events. Fretting corrosion can cause damage to or failure of the implant itself. Cobalt-chromium associated metallosis can cause an adverse local tissue reaction that can lead to bone and tissue damage. An allergic biologic response to nickel can occur with stainless steel implants. Further, it can be difficult to predict how a patient will respond to metal debris prior to implantation and symptoms of adverse reactions to metal debris can take many months to years to appear after implantation. It is therefore desirable to provide implants that reduce or eliminate the potential for the occurrence of such adverse events.

SUMMARY

This section provides a general summary of the disclosure, and is not a comprehensive disclosure of its full scope or all of its features.

The present inventors have recognized that eliminating cobalt-chromium or stainless steel in implant junctions or interfaces while still using these materials for their desired properties outside of these regions can reduce the potential for patient complications resulting from cobalt chromium, or nickel metal debris. Implants and methods for manufacturing composite implants without junctions that are comprised of cobalt chromium or stainless steel would therefore be desirable. Accordingly, the present teachings provide for junctionless monolithic composite implants and methods for manufacturing the same. The implant can comprise a monolithic composite body having a first region comprising a first metal alloy, a second region comprising a second metal alloy, and a transition region disposed between the first region and the second region comprising a bonded mixture of the first alloy and the second alloy. In one example, the transition region can comprise a sintered mixture of the first alloy and the second alloy. In another example, the transition region can be disposed at a region of minimum stress within the monolithic composite body under physiological loading conditions of the implant. In an additional or alternative example, the transition region can define an interlocked geometry between the first region and the second region. The transition zone can also be located to allow for a minimum thickness of material of either or both alloys as needed to maintain required wear and/or fatigue performance.

In another example, a method of manufacturing a junctionless, monolithic composite implant comprises the steps of determining the design of an implant; optimizing the design of the implant to at least determine a region of minimum stress within an implant under physiological loading conditions; defining a transition region between a first metal alloy and a second metal alloy substantially coincident with the region of minimum stress; inputting manufacturing instructions for the optimized implant and transition region into an additive manufacturing machine; and selectively bonding individual particles of either or both of the first metal alloy and the second metal alloy in accordance with the additive manufacturing instructions to form a monolithic composite implant.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

The present teachings provide for junctionless monolithic composite implants, and methods for manufacturing the same. Such implants can reduce the potential for patient complications by eliminating a source of metal debris from implants where different metal alloys for different features of the implant are desirable. In one exemplary implementation, the implant can comprise a junctionless monolithic composite femoral head. However, it should be understood that this disclosure encompasses numerous other implants including, but not limited to, endo hip heads, unipolar hip heads, hip femoral stems, knee femoral components and compatible stem extensions, knee tibial trays and compatible stem extensions, shoulder heads and compatible stem extensions, elbow prosthetic components such as radial head implants, and the like.

Figure 1:
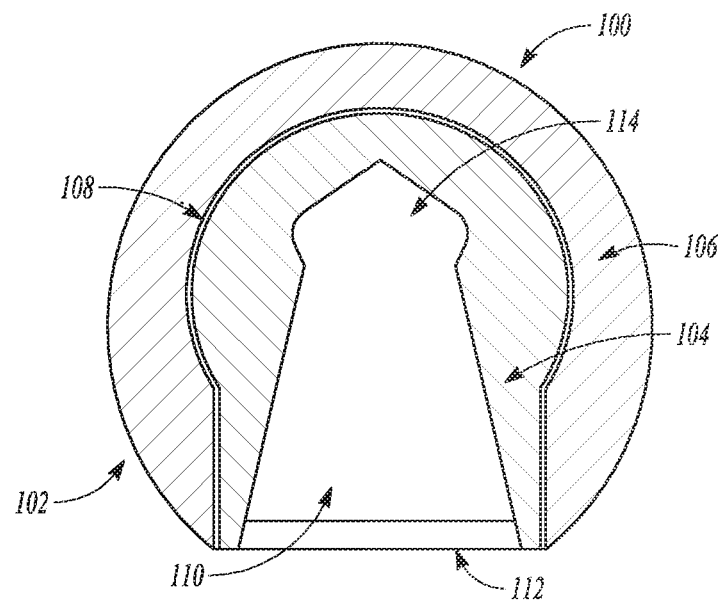
FIG. 1 illustrates a cross-sectional view of a junctionless monolithic composite implant according to an exemplary embodiment of the present disclosure.

With reference to FIG. 1, an implant 100 can comprise a monolithic (or monoblock) composite body 102 having a first region 104, a second region 106, and a transition region 108 disposed between the first region 104 and the second region 106.

The first region 104 can comprise a first metal alloy and the second region 106 can comprise a second metal alloy. The transition region 108 can comprise a bonded mixture of the first alloy and the second alloy. In one example, the transition region 108 can comprise a sintered mixture of the first alloy and the second alloy. The first alloy can be selected to ensure biocompatibility, avoidance of metal sensitivity, adequate fatigue strength, corrosion (e.g., fretting corrosion) resistance, and manufacturability. The first alloy can comprise a titanium alloy. The second alloy can be selected to ensure biocompatibility, wear performance, adequate fatigue strength, and manufacturability. The second alloy can comprise one of, for example and without limitation, stainless steel, cobalt-chromium (CoCr), and titanium (Ti) alloy. An alloy comprising Ti can further comprise a hardenable Ti alloy.

In one example, the geometry and location of the transition region 108 can be selected to optimize the femoral head wear and fatigue performance. Here, the geometry of the transition region 108 can be selected to ensure that the zone of articulation is within the surface area of the second region 106. In an additional or alternative example, the geometry of the transition region 108 can be selected to ensure that that the thickness of the second metal alloy at a selected hardness value is sufficient to avoid wear through the second region 106 or a stress state that could result in fracture of the wear surface or of second region 106.

In another example, the transition region 108 can be isolated from the environment in the body when the implant 100 is in an implanted configuration. In an additional or alternative example, the transition region 108 can be completely internal to the monolithic composite body 102 (i.e., no portion of the transition region is exposed on the exterior surface of the monolithic composite body). In either case, the transition region 108 can be isolated from the environment in the body when the implant is implanted in order to reduce or eliminate the potential for galvanic corrosion at or about the transition region 108.

In another example, the transition region 108 can be disposed at a region of minimum stress within the monolithic composite body 102 under physiological loading conditions of the implant 100. In one example, finite element analysis can be used to map stress in the monolithic composite body and the transition region 108 can be determined based thereon.

Figure 2:
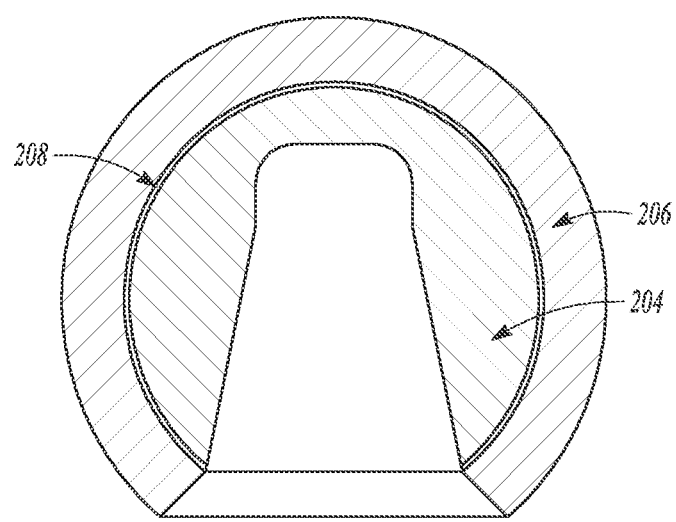
FIG. 2 illustrates a cross-sectional view of another junctionless monolithic composite implant according to an exemplary embodiment of the present disclosure.
Figure 3:
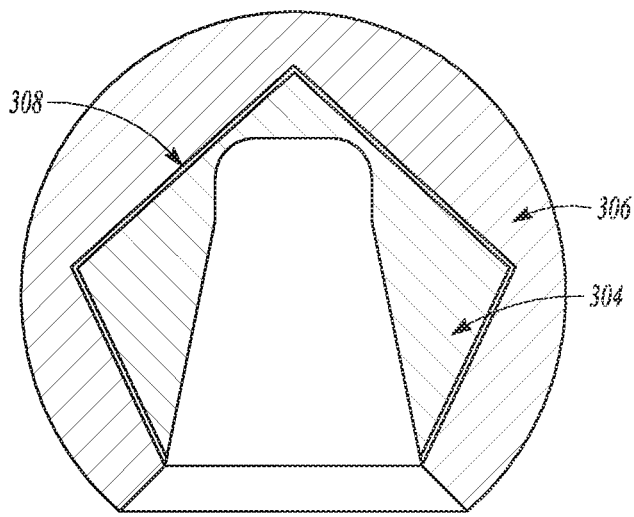
FIG. 3 illustrates a cross-sectional view of another junctionless monolithic composite implant according to an exemplary embodiment of the present disclosure.

In another example, the transition region 108 can define an interlocked geometry between the first region 104 and the second region 106. The interlocked geometry can be a secondary mechanical or geometric lock between the first region 104 and the second region 106. As illustrated in FIG. 1, the transition region 108 can circumscribe a three-dimensional shape having a keyhole-shaped cross-section such that an outer boundary of the first region 104 is interlocked with the complementary inner boundary of the second region 106. In another example illustrated in FIG. 2, the transition region 208 disposed between the first region 204 and the second region 206 can be substantially spherical such that an outer boundary of the first region 204 circumscribes a sphere that is interlocked with an inner boundary of the second region 206 that defines a complementary sphere. In another example illustrated in FIG. 3, the transition region 308 disposed between the first region 304 and the second region 306 can be shaped such that an outer boundary of the first region 304 circumscribes a polyhedron that is interlocked with an inner boundary of the second region 306 defining a mating polyhedron.

In one exemplary example, the monolithic composite body 102 can comprise a femoral head. The first region 104 can comprise a cobalt-chromium (CoCr) alloy, the second region 106 can comprise a titanium (Ti) alloy, and the transition region 108 can comprise a sintered mixture of the Ti alloy and the CoCr alloy.

In another example, the monolithic composite body 102 can have voids selectively disposed within the monolithic composite body 102 in order to, e.g., reduce the weight of the implant.

The first region 104 can have a bore 110 disposed therein and the bore 110 can be tapered from an exterior surface 112 of the first region 104 inward. A bottom surface of the bore 110 can have a counter bore 114 disposed therein. The geometry of the counter bore 114 can be determined at least partially based on the designed stress state of the femoral head.

Figure 4:
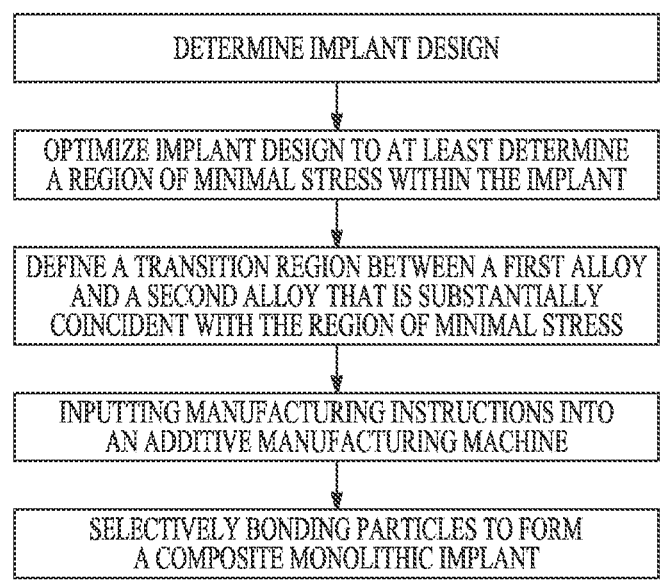
FIG. 4 is a flow chart illustrating an exemplary method of manufacturing a junctionless monolithic composite implant.

In another example illustrated in FIG. 4, a method of manufacturing a functionless composite monolithic implant can comprise the steps of: determining the design of an implant (step 402); optimizing the design of the implant to determine a region of minimum stress within the implant under physiological loading conditions (step 404), defining a transition region between a first metal alloy and a second metal alloy that is substantially coincident with the region of minimum stress (step 406); inputting manufacturing instructions for the optimized implant and the transition region into an additive manufacturing machine (step 408); selectively bonding individual particles of either or both of the first metal alloy and the second metal alloy in accordance with the additive manufacturing instructions to form a monolithic composite implant (step 410). In one example, selectively bonding the individual particles comprises sintering the individual particles. In one example, a plurality of monolithic composite implants can be manufactured simultaneously in a single additive manufacturing machine. In another example, individual monolithic composite implants can be attached to a build plate via struts created during the additive manufacturing process in order to avoid deformation or fracture during the additive manufacturing process. Optionally, the monolithic composite implant can be annealed or otherwise hardened post-additive manufacturing.

Optionally, additional features can be machined in the monolithic composite implant post-additive manufacturing. In one example, the bore 110 can be included in the additive manufacturing instructions and at least partially formed during the additive manufacturing process. The geometry of the bore 100 can be finalized via machining. In another example, the bore 110 can be machined into the first region 104. In another example, the geometry of the counter bore 114 can be determined based on the manufacturing process for the bore 110.

Optionally, post-additive manufacturing, the monolithic composite implant can undergo a surface treatment such as, for example and without limitation, polishing, coating, and the like. In one example, at least a portion of an external surface of the monolithic composite implant can be at least one of polished and buffed. In another example, at least a portion of an external surface of the monolithic composite implant can be coated with another substance. Coating the surface of the monolithic composite implant can further comprise applying a porous coating to at least a portion of an external surface of the monolithic composite implant.

Some numbered examples of the present disclosure follow:

Example 1 is an implant, comprising: a monolithic composite body that can have a first region comprising a first metal alloy, a second region comprising a second metal alloy, and a transition region disposed between the first region and the second region. The transition region can comprise a sintered mixture of the first metal alloy and the second metal alloy.

In Example 2, the subject matter of Example 1 optionally includes wherein the first metal alloy comprises a titanium alloy.

In Example 3, the subject matter of Example 2 optionally includes wherein the second metal alloy comprises one of a cobalt chromium alloy, stainless steel, and a titanium alloy.

In Example 4, the subject matter of any one or more of Examples 1-3 optionally include, wherein the transition region is internal to the monolithic composite body.

In Example 5, the subject matter of any one or more of Examples 1-4 optionally include, wherein the transition region is disposed at a region of minimum stress within the monolithic composite body under physiological loading conditions of the implant.

In Example 6, the subject matter of any one or more of Examples 1-5 optionally include, wherein the transition region defines an interlocked geometry between the first region and the second region.

Example 7 is an implant, comprising: a monolithic femoral head that can have: a first region formed from a first metal alloy; a second region formed from a second metal alloy and comprising a core and an articulating surface; and a transition region disposed between the first region and the second region. The transition region can comprise a sintered mixture of the first metal alloy and the second metal alloy.

In Example 8, the subject matter of Example 7 optionally includes wherein the transition region is disposed at an area of minimum stress within the monolithic femoral head under physiological loading conditions.

In Example 9, the subject matter of any one or more of Examples 7-8 optionally include, wherein the transition region defines an interlocked geometry between the first region and the second region.

In Example 10, the subject matter of any one or more of Examples 7-9 optionally include, wherein the first metal alloy is a titanium alloy.

In Example 11, the subject matter of Example 10 optionally includes wherein the second metal alloy is one of stainless steel, a cobalt chromium alloy, and a titanium alloy.

In Example 12, the subject matter of any one or more of Examples 7-11 optionally include, wherein the transition region is not exposed on an exterior surface of the monolithic femoral head.

In Example 13, the subject matter of any one or more of Examples 7-12 optionally include wherein the first region has a bore disposed therein.

In Example 14, the subject matter of Example 13 optionally includes wherein the bore is tapered from an exterior surface of the first region inward.

In Example 15, the subject matter of any one or more of Examples 13-14 optionally include wherein the bore further comprises a counterbore disposed in a bottom surface of the bore.

Example 16 is a method of manufacturing an implant, comprising: determining a design of an implant; optimizing the design of the implant to at least determine a region of minimum stress within the implant under physiological loading conditions; defining a transition region between a first metal alloy and a second metal alloy substantially coincident with the region of minimum stress; inputting manufacturing instructions for the optimized implant and transition region into an additive manufacturing machine; and selectively bonding individual particles of either or both of the first metal alloy and the second metal alloy in accordance with the additive manufacturing instructions to form a monolithic composite implant.

In Example 17, the subject matter of Example 16 optionally includes wherein selectively bonding the individual particles of both of the first metal alloy and the second metal alloy in the transition region comprises sintering the individual particles of both of the first metal alloy and the second metal alloy.

In Example 18, the subject matter of any one or more of Examples 16-47 optionally include the step of annealing the monolithic composite implant.

In Example 19, the subject matter of any one or more of Examples 16-48 optionally include machining an additional feature in the monolithic composite implant.

In Example 20, the subject matter of any one or more of Examples 16-49 optionally include at least one of polishing or buffing at least a portion of an outer surface of the monolithic composite implant.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b) at the time of filing this application, to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A method of manufacturing an implant, comprising:
    determining a design of an implant;
    optimizing the design of the implant to at least determine a region of minimum stress within the implant under physiological loading conditions;
    defining a transition region between a first metal alloy and a second metal alloy substantially coincident with the region of minimum stress;
    inputting manufacturing instructions for the optimized implant and transition region into an additive manufacturing machine; and
    selectively bonding individual particles of either or both of the first metal alloy and the second metal alloy in accordance with the additive manufacturing instructions to form a monolithic composite implant.

2. The method of claim 1, wherein selectively bonding the individual particles of both of the first metal alloy and the second metal alloy in the transition region comprises sintering the individual particles of both of the first metal alloy and the second metal alloy.

3. The method of claim 1, further comprising the step of annealing the monolithic composite implant.

4. The method of claim 1, further comprising machining an additional feature in the monolithic composite implant.

5. The method of claim 1, further comprising at least one of polishing or buffing at least a portion of an outer surface of the monolithic composite implant.

6. The method of claim 1, wherein the first metal alloy comprises a titanium alloy.

7. The method of claim 6, wherein the second metal alloy comprises one of a cobalt chromium alloy, stainless steel, and a titanium alloy.

8. The method of claim 1, wherein the transition region is internal to the monolithic composite implant.

9. The method of claim 1, wherein the transition region defines an interlocked geometry between the first metal alloy and the second metal alloy.

10. The method of claim 1, wherein the transition region comprises a sintered mixture of the first metal alloy and the second metal alloy.

11. The method of claim 1, wherein selectively bonding individual particles of either or both of the first metal alloy and the second metal alloy creates voids within the monolithic composite implant to reduce the weight of the implant.

12. The method of claim 1, wherein the transition region is substantially spherical.

13. A method of manufacturing an implant, comprising:
    determining a design of an implant;
    defining a transition region between a first metal alloy and a second metal alloy;
    inputting manufacturing instructions for the implant and transition region into an additive manufacturing machine; and
    selectively bonding individual particles of either or both of the first metal alloy and the second metal alloy in accordance with the additive manufacturing instructions to form a monolithic composite implant.

14. The method of claim 13, wherein determining the design of the implant further comprises optimizing the design of the implant to at least determine a region of minimum stress within the implant under physiological loading conditions.

15. The method of claim 14, wherein the transition region is substantially coincident with the region of minimum stress.

16. The method of claim 13, wherein selectively bonding the individual particles of both of the first metal alloy and the second metal alloy in the transition region comprises sintering the individual particles of both of the first metal alloy and the second metal alloy.

17. The method of claim 13, wherein the transition region comprises a sintered mixture of the first metal alloy and the second metal alloy.

18. The method of claim 13, further comprising the step of annealing the monolithic composite implant.

19. The method of claim 13, further comprising machining an additional feature in the monolithic composite implant.

20. The method of claim 13, wherein the monolithic composite implant includes a bore formed therein.

* * * * *